(12) United States Patent
Toyama et al.

(10) Patent No.: US 7,910,745 B2
(45) Date of Patent: Mar. 22, 2011

(54) ORGANIC COMPOUND AND METHOD FOR PRODUCING RADIOACTIVE HALOGEN-LABELED ORGANIC COMPOUND USING THE SAME

(75) Inventors: Masahito Toyama, Sodegaura (JP); Fumie Kurosaki, Sodegaura (JP); Akio Hayashi, Sodegaura (JP); Osamu Ito, Sodegaura (JP)

(73) Assignee: Nihon Medi-Physics Co., Ltd., Tokyo (JP)

( * ) Notice: Subject to any disclaimer, the term of this patent is extended or adjusted under 35 U.S.C. 154(b) by 237 days.

(21) Appl. No.: 11/915,267

(22) PCT Filed: May 15, 2006

(86) PCT No.: PCT/JP2006/309643
§ 371 (c)(1),
(2), (4) Date: Nov. 21, 2007

(87) PCT Pub. No.: WO2006/126410
PCT Pub. Date: Nov. 30, 2006

(65) Prior Publication Data
US 2009/0105489 A1    Apr. 23, 2009

(30) Foreign Application Priority Data

May 23, 2005   (JP) ................................ 2005-149186

(51) Int. Cl.
*C07D 285/01*   (2006.01)
*C07D 207/404*  (2006.01)
*C07D 209/48*   (2006.01)
*C07C 61/04*    (2006.01)

(52) U.S. Cl. .......... 548/123; 548/479; 548/547; 562/505

(58) Field of Classification Search .................. None
See application file for complete search history.

(56) References Cited

U.S. PATENT DOCUMENTS 5,808,146 A   9/1998  Goodman
5,817,776 A  10/1998  Goodman

FOREIGN PATENT DOCUMENTS

| JP | 2000-500442 A | 1/2000 |
| WO | WO97/17092 A | 5/1997 |
| WO | WO-2004/056725 A1 | 7/2004 |

OTHER PUBLICATIONS

Greene et al. Protective Groups in Organic Synthesis, Chap. 7, 3$^{rd}$ ed. Published Online Apr. 23, 2002.*
McConathy et al. "Improved synthesis of anti-[18-F]FACBC: improved preparation of labeling precursor and automated radiosynthesis." Applied Radiation and Isotopes, 58 (2003) pp. 657-666.*
Ren. "Reactions for Medicine Synthesis." Chemical Industry Press, 1$^{st}$ Ed. (1988), p. 149.*
Shoup and Goodman. J. Labelled Cpd. Radiopharm. 42, 215-224 (1999).*
McConathy, Improved synthesis of anti[19F]FACBC: improved preparation of labeling precursor and automated radiosynthesis, Applied Radiation and Isotopes, 58(6):657-666 (2003).
Shoup et al, Synthesis of [F—18]—1-3-fluorocyclobutane-1-cargboxylic acid (FACBC): a PET tracer for tumor delineation, Journal of Labelled Compounds & Radiopharmaceuticals, 42(3):215-225 (1999).
English translation of Chinese Official Action issue don Feb. 5, 2010 in Chinese Application No. 200680017927.X.
REN "Ractions for Medicine Synthesis". Chemical Press, First Edition (1988), p. 149.
PCT International Preliminary Report on Patentability in PCT/JP2006/309643, dated Nov. 23, 2007.
PCT Written Opinion of the International Searching Authority in PCT/JP2006/309643, dated Nov. 23, 2007.
Office Action dated Oct. 1, 2010, in Russian application 200812677.
Laurent Martarelli, et al., Synthesis of *syn-* and *anti*-1 -Amino-3-[$^{18}$F]fluoromethyl-cyclobutane-1-carboxylic Acid (FMACBC), Potential PET Ligands for Tumor Detection, Journal of Medical Chemistry, Apr. 26, 2002, pp. 2250-2259, vol. 45, No. 11, American Chemical Society.
Office Action dated Nov. 15, 2010 in Chinese application 200680017927.X , in Chinese accompanied by English language translation.

* cited by examiner

*Primary Examiner* — Rebecca L Anderson
*Assistant Examiner* — Alicia L Otton
(74) *Attorney, Agent, or Firm* — Fitch, Even, Tabin & Flannery

(57) ABSTRACT

It is intended to provide a labeling precursor compound used for selectively producing radioactive halogen-substituted syn-1-amino-3-cyclobutane-carboxylic acids, and to provide a process for producing a radioactive halogen-substituted syn-1-amino-3-cyclobutane-carboxylic acid using the labeling precursor compound. A labeling precursor is used in which a phthalimide group is used as a protective group for protecting the amino group. The syn-form of the radioactive halogen-substituted 1-amino-3-cyclobutane-carboxylic acid can be selectively produced by labeling the labeling precursor with a radioactive halogen followed by deprotecting.

16 Claims, 2 Drawing Sheets

1) sat.Ba(OH)$_2$ aq., reflux, 20h; 2) Et$_3$N, phthalic anhydride, toluene, reflux, 5h; 3) (trimethylsilyl)diazomethane, MeOH:THF = 1:1, rt., 3h (3steps 78%); 4) palladium-activated carbon, MeOH, rt., 5h(87%); 6) pyridine, trifluoromethanesulfonyl anhydride, 0°C, 30min(92%).

1) Et$_3$N·3HF, Et$_3$N, 1,2-dichloroethane, reflux, 3h(97%)

2) hydrazine hydrate, 75°C, 2h(75%)

1) Kryptofix2.2.2, K$_2$CO$_3$, 80°C, 15min; 2) hydrazine hydrate, 75°C, 10min.

ORGANIC COMPOUND AND METHOD FOR PRODUCING RADIOACTIVE HALOGEN-LABELED ORGANIC COMPOUND USING THE SAME

This Application is the U.S. National Stage Application under 35 U.S.C. 371 of International Application PCT/JP/2006/309643 filed May 15, 2006 which claims benefit of and foreign priority from Japanese patent application number 2005-149186 filed May 23, 2005, the complete disclosures of which are incorporated herein by reference.

TECHNICAL FIELD

The present invention relates to an organic compound which can be effectively used as a precursor for production of radioactive halogen-labeled organic compounds, and a process for producing radioactive halogen-labeled organic compounds using the same.

BACKGROUND ART

Nuclear medicine examination represented by positron emission tomography (hereinafter referred to as PET) and single photon emission computed tomography (hereinafter referred to as SPECT), is effective in diagnosing a variety of diseases including heart disease and cancer. These techniques involve administering an agent labeled with a specific radioisotope (hereinafter referred to as radiopharmaceutical) to a patient, followed by detecting γ-rays emitted directly or indirectly from the agent. Nuclear medicine examination is characteristic in that it has not only high specificity and sensitivity to diseases, but also an advantage of providing information on the functioning of lesions, compared to other examination techniques.

For example, [$^{18}$F]2-fluoro-2-deoxy-D-glucose (hereinafter referred to as "$^{18}$F-FDG"), one of radiopharmaceuticals used for PET examination, tends to be concentrated in area where glucose metabolism is enhanced, thereby making it possible to specifically detect tumors in which glucose metabolism is enhanced.

Nuclear medicine examination is performed by tracing a distribution of an administered radiopharmaceutical, and data obtained therefrom vary depending on nature of the radiopharmaceutical. Thus, different radiopharmaceuticals have been developed for different diseases, and some of them are put into clinical use. There have been developed, for example, various tumor diagnostic agents, bloodstream diagnostic agents and receptor mapping agents.

In recent years, a series of radioactive halogen-labeled amino acid compounds including [$^{18}$F]-1-amino-3-fluorocyclobutanecarboxylic acid (hereinafter referred to as [$^{18}$F]-FACBC) have been designed as novel radiopharmaceuticals, and their clinical application is under examination (Patent Document 1, and non-Patent Document 1). [$^{18}$F]-FACBC is considered to be effective as a diagnostic agent for highly proliferative tumors, because it has a property of being taken up specifically by amino acid transporter.

Patent Document 1: Japanese Patent Laid-open No. 2000-500442.

Non-Patent Document 1: Jonathan McConathy et al., "Improved synthesis of anti-[18F]FACBC: improved preparation of labeling precursor and automated radiosynthesis.", Applied Radiation and Isotopes, (Netherlands), 2003, 58, p. 657-666.

DISCLOSURE OF THE INVENTION

Problems to be Solved by the Invention

There are two stereoisomers, namely, an anti-form and a syn-form of radioactive halogen-labeled 1-amino-3-halocyclobutane-carboxylic acids including [$^{18}$F]-FACBC, from the viewpoint of structure. In both of the above Patent Document 1 and non-Patent Document 1, however, there is no disclosure of processes for selectively producing the syn-form but the anti-form.

The present invention has been made in light of the above described circumstances. Accordingly, an object of the present invention is to provide a labeling precursor compound for selectively producing radioactive halogen-labeled syn-1-amino-3-halocyclobutane-carboxylic acids including syn-[$^{18}$F]-FACBC, and a process for producing a radioactive halogen-labeled syn-1-amino-3-halocyclobutane-carboxylic acid using the precursor compound.

Means for Solving the Problems

As a result of intensive researches, the present inventors have found that a labeling precursor in which an amino group is protected by a cyclic imide group makes it possible to selectively produce radioactive halogen-labeled syn-1-amino-3-halocyclobutane-carboxylic acids. Thus, the present invention has been finally accomplished.

According to one aspect of the present invention, there is provided an organic compound represented by the following formula (1):

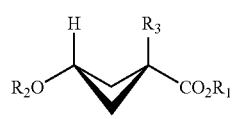

(1)

wherein $R_1$ is a straight-chain or branched-chain alkyl group with one to 10 carbon atoms or an aromatic substituent; $R_2$ is a straight-chain or branched-chain haloalkylsulfonic acid substituent with one to 10 carbon atoms, a straight-chain or branched-chain alkylsulfonic acid substituent with one to 10 carbon atoms, or an aromatic sulfonic acid substituent; and $R_3$ is a cyclic imide substituent.

According to another aspect of the present invention, there is provided a process for producing a radioactive halogen-labeled organic compound comprising the steps of:
incorporating a radioactive halogen atom into the carbon atom at position 3 of a labeling precursor compound represented by the following formula (1):

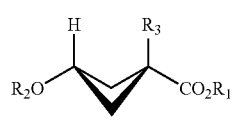

(1)

wherein $R_1$ is a straight-chain or branched-chain alkyl group with one to 10 carbon atoms, or an aromatic substituent; $R_2$ is a straight-chain or branched-chain haloalkylsulfonic acid substituent with one to 10 carbon atoms, a straight-chain or branched-chain alkylsulfonic acid substituent with one to 10 carbon atoms, or an aromatic sulfonic acid substituent; and $R_3$ is a cyclic imide substituent, to obtain a compound represented by the following formula (2):

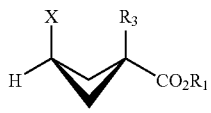

(2)

wherein X is a radioactive halogen substituent; $R_1$ is a straight-chain or branched-chain alkyl chain with one to 10 carbon atoms, or an aromatic substituent; and $R_3$ is a cyclic imide substituent; and deprotecting the above obtained compound to yield a compound represented by the following formula (3):

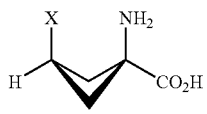

(3)

wherein X represents a radioactive halogen substituent.

In the above formula (1), $R_1$, represents a straight-chain or branched-chain alkyl group with one to 10 carbon atoms or an aromatic substituent. Among them, a substituent which is selected from the group consisting of methyl, ethyl, t-butyl and phenyl groups can be preferably used.

In the above formula (1), $R_2$ represents a substituent selected from the group consisting of straight-chain or branched-chain haloalkylsulfonic acid substituents with one to 10 carbon atoms, straight-chain or branched chain alkylsulfonic acid substituents with one to 10 carbon atoms and aromatic sulfonic acid substituents. Of these, a substituent which is selected from the group consisting of methanesulfonic acid, toluenesulfonic acid, nitrobenzenesulfonic acid, benzenesulfonic acid, trifluoromethanesulfonic acid, fluorosulfonic acid and perfluoroalkylsulfonic acid can be preferably used.

In the above formula (1), $R_3$ is a cyclic imide substituent, that is, a residue formed by removal of a hydrogen from a compound represented by the general formula (8): $R_4$—CONHCO—$R_5$ (wherein $R_4$ and $R_5$ bind to each other to form a ring). Accordingly, the nitrogen atom shown in the general formula (8) is bound to the carbon atom at position 1 of the cyclobutane ring shown in the general formulae (1) and (2). In the above general formula (8), $R_4$ and $R_5$ are preferably a carbon or sulfur atom and preferably form a 5-membered cyclic imide by linkage to each other. $R_4$ and $R_5$ may optionally have a substituent as long as they bind to each other. Specifically, as the cyclic imide substituent, may be used a carbocyclic dicarboximide, saturated aliphatic dicarboximide or unsaturated aliphatic dicarboximide.

As a carbocyclic dicarboximide, various kinds of compounds can be used. However, preferably one selected from the group consisting of phthalimide, halogenated phthalimide, nitrophthalimide, 1,2-cyclopropanecarboximide, 1,2-cyclopentanecarboximide, 1,2-cyclohexanecarboximide, and isoquinoline-1,3-dione is used, more preferably phthalimide, tetrachlorophthalimide, tetrafluorophthalimide or 4-nitrophthalimide is used, and particularly preferably phthalimide is used.

As a saturated aliphatic dicarboximide, various kinds of compounds can be used. However, preferably one selected from the group consisting of succinimide, dithiosuccinimide and glutarimide is used, and more preferably dithiosuccinimide is used.

As an unsaturated aliphatic dicarboximide, various kinds of compounds can be used. However, preferable are various maleimides, and more preferable is 2,3-diphenylmaleimide.

In a process for producing radioactive halogen-labeled organic compounds according to the present invention, the above described deprotection may be carried out by any method, as long as a cyclic imide substituent is converted into a primary amine substituent and a carboxylic acid ester substituent is converted into a carboxylic acid.

Specifically, the above described deprotection can be achieved by exposing a solution containing a compound represented by the above formula (2) to an acidic condition. Any method can be employed as long as it allows the solution to be exposed to an acidic condition; however, a method can be preferably used in which an acid is added to the solution containing a compound represented by the above formula (2). As an acid, one selected from the group consisting of hydrochloric acid, sulfuric acid, methanesulfonic acid, formic acid and acetic acid can be preferably used here.

Alternatively, the above described deprotection can be carried out by employing a method which includes the steps of: subjecting a solution containing a compound represented by the above formula (2) to a reducing condition so as to deprotect the cyclic imide protective group; and then carrying out hydrolysis so as to deprotect the carboxylic acid ester. Various methods can be employed to subject the solution to a reducing condition. One preferred method is, for example, to add a reducing agent to the solution containing a compound represented by the above formula (2). As a reducing agent, one selected from the group consisting of hydrazine, methylhydrazine, phenylhydrazine, ethylenediamine and sodium borohydride can be preferably used here.

Hydrolysis can be performed in accordance with widely used hydrolytic procedures. This step may be carried out by adding the above described reducing agent together with water to the reaction solution concurrently with the step of deprotecting the cyclic imide protective group.

EFFECTS OF THE INVENTION

By use of the organic compound according to the present invention and of the production process utilizing the organic compound, it has been made possible to selectively produce radioactive halogen-labeled syn-1-amino-3-halocyclobutane-carboxylic acids.

BEST MODE FOR CARRYING OUT THE INVENTION

Hereinafter, a process for producing a compound of the present invention will be described taking, as an example, anti-1-(N-phthalimide)-3-[[(trifluoromethyl)sulfonyl]oxy]-cyclobutane-1-carboxylic acid methyl ester.

First, a solution prepared by dissolving anti-5-(3-benzyloxycyclobutane)hydantoin in a saturated barium hydroxide solution is refluxed, and sulfuric acid is then added to the solution to adjust the pH of the same to about 7. The solution is then filtered, and the filtrate is concentrated to allow anti-1-(N-amino)-3-benzyloxycyclobutane-1-carboxylic acid to precipitate as white crystals. The acid used for the pH adjustment may be an acid other than sulfuric acid, but is desirably an acid that forms a water-insoluble inorganic salt with barium.

The resultant anti-1-amino-3-benzyloxycyclobutane-1-carboxylic acid is dissolved in an organic solvent having a high boiling point. Then, the solution is supplemented with phthalic anhydride in an atmosphere of argon and heated under reflux to allow the reaction to progress. Then, the reaction solution is concentrated to yield anti-1-(N-phthalimide)-3-benzyloxycyclobutane-1-carboxylic acid as oily matter. As an organic solvent in which anti-1-amino-3-benzyloxycyclobutane-1-carboxylic acid is dissolved, any organic solvent can be used as long as it is an organic solvent having a boiling point that is sufficiently high to allow water to be azeotropically distilled off. Preferred examples thereof include an aromatic hydrocarbon such as dehydrated toluene and dimethylformamide. The amount of phthalic anhydride to be added is desirably equivalent to or larger than the substrate.

In the above described reaction step, preferably a base such as triethylamine is added together with phthalic anhydride so as to allow the reaction to progress more rapidly. The amount of the base, such as triethylamine, to be added is not restricted as long as it is larger than the catalytic amount. For example, the amount equal to or larger than 0.1 equivalent of the substrate is sufficient.

To a solution prepared by dissolving the yielded anti-1-(N-phthalimide)-3-benzyloxycyclobutane-1-carboxylic acid in a mixed solution of dehydrated methanol/dehydrated tetrahydrofuran (1:1), (trimethylsilyl)diazomethane is added in an amount equal to or larger than 1 equivalent of the substrate and stirred at room temperature to allow them to react. The reaction solution is purified and concentrated to yield anti-1-(N-phthalimide)-3-benzyloxycyclobutane-1-carboxylic acid methyl ester (the following formula (4)).

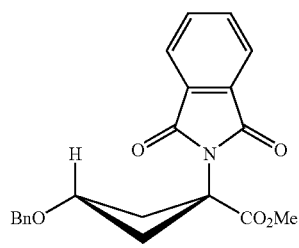

(4)

To a solution prepared by dissolving the anti-1-(N-phthalimide)-3-benzyloxycyclobutane-1-carboxylic acid methyl ester synthesized above in an alcohol solvent such as ethanol or an acetate ester solvent such as ethyl acetate ester, palladium-on-activated carbon (amount: 10 w/w % or more relative to the substrate) is added in an atmosphere of hydrogen and allowed to react under stirring at room temperature. The reaction solution is then filtered through Celite, and the filtrate is concentrated and purified to yield anti-1-(N-phthalimide)-3-hydroxycyclobutane-1-carboxylic acid methyl ester (the following formula (5)).

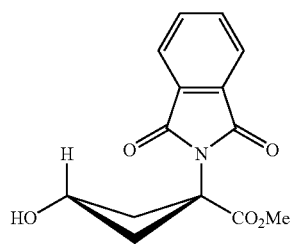

(5)

The anti-1-(N-phthalimide)-3-hydroxycyclobutane-1-carboxylic acid methyl ester synthesized above is dissolved in a halogenated hydrocarbon such as dehydrated methylene chloride or an ether such as diethyl ether and allowed to react with a base, such as pyridine, and trifluoromethane anhydride in an atmosphere of argon. To this reaction solution, water and an acid are added and allowed to stand so as to undergo separation. The resultant organic layer is purified and concentrated to yield anti-1-(N-phthalimide)-3-[[(trifluoromethyl)sulfonyl]oxy]-cyclobutane-1-carboxylic acid methyl ester (the following formula (6)).

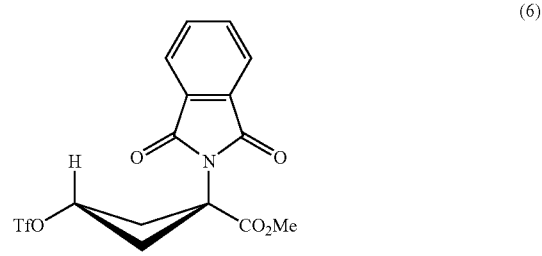

(6)

Next, a process for producing radioactive halogen-labeled organic compounds in accordance with the present invention will be described referring to an example in which syn-[$^{18}$F]-FACBC is produced using, as a labeling precursor, anti-1-(N-phthalimide)-3-[[(trifluoromethyl)sulfonyl]oxy]-cyclobutane-1-carboxylic acid methyl ester.

The production of syn-[$^{18}$F]-FACBC is performed through the following two steps: a step of adding radioactive fluorine to the precursor; and a step of deprotecting the precursor compound to which radioactive fluorine has been added.

Radioactive fluorine can be obtained by a known method, for example, a method in which $H_2^{18}O$ enriched water is used as a target and exposed to proton bombardment. In this instance, radioactive fluorine exists in the $H_2^{18}O$ enriched water used as a target. The $H_2^{18}O$ enriched water containing radioactive fluorine is allowed to pass through an anion-exchange column so that radioactive fluorine is adsorbed and collected on the column, thereby being separated from the $H_2^{18}O$ enriched water. Thereafter, a potassium carbonate solution is allowed to pass through the column to elute radioactive fluorine, and the eluate is supplemented with a phase transfer catalyst and is evaporated to dryness, thereby activating radioactive fluorine.

Then, the dried radioactive fluorine is dissolved in acetonitrile, and the acetonitrile solution is added to the anti-1-(N-phthalimide)-3-[[(trifluoromethyl)sulfonyl]oxy]-cyclobutane-1-carboxylic acid methyl ester, as a precursor, to allow them to react under heating. As a result, radioactive fluorine is added to the precursor compound, whereby syn-1-(N-phthalimide)-3-[$^{18}$F]fluorocyclobutane-1-carboxylic acid methyl ester shown in the following formula (7) is synthesized.

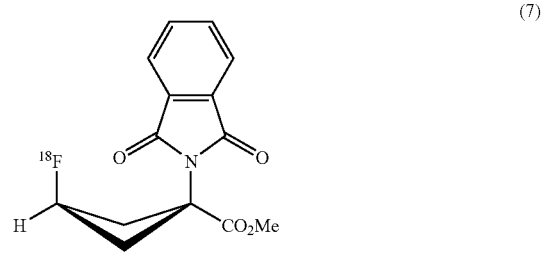

(7)

Syn-[$^{18}$F]-FACBC, as a target compound, can be obtained in a single step if deprotection is conducted by, for example, exposing the resultant syn-1-(N-phthalimide)-3-[$^{18}$F]fluorocyclobutane-1-carboxylic acid methyl ester to an acidic condition. The acidic condition can be provided by various methods, for example, a method in which an acid is added to a solution that contains the syn-1-(N-phthalimide)-3-[$^{18}$F] fluorocyclobutane-1-carboxylic acid methyl ester. The amount of the acid to be added need not be restricted as long as the amount can provide a condition that is acidic sufficiently to perform the deprotection. Preferably, the amount is equal to or larger than 3 equivalents of the substrate.

Instead of the method in which deprotection is conducted under the acidic condition, a method may also be used in which the imide protective group is first deprotected under a reducing condition and then the ester is deprotected by hydrolysis.

Hereinafter, the present invention will be described in further detail with reference to Examples; however, it should be understood that the details of the Examples are not intended to limit the present invention.

The NMR used in the Examples was measured by nuclear magnetic resonance spectrometer manufactured by JEOL Ltd. (type: JNM-ECP-500, resonance frequency: 500 MHz), and the chemical shift values were shown in ppm. In NMR measurement using CDCl$_3$ as a solvent, tetramethylsilane was used as an internal standard.

As the fillers in column chromatography, Silica Gel 60N (under trade name, manufactured by KANTO CHEMICAL Co., Inc.) was used. The column used in preparative HPLC was CAPCELL PAK C$_{18}$ UG805 μm (under trade name, manufactured by SHISEIDO Co., Ltd., size: 15 mmϕ×250 mm).

Example 1

Synthesis of anti-1-(N-phthalimide)-3-[[(trifluoromethyl)sulfonyl]oxy]-cyclobutane-1-carboxylic acid methyl ester A synthetic scheme for anti-1-(N-phthalimide)-3-[[(trifluoromethyl)sulfonyl]oxy]-cyclobutane-1-carboxylic acid methyl ester is shown in FIG. 1.

Anti-5-(3-benzyloxycyclobutane)hydantoin was synthesized in accordance with the method described in a document (Jonathan McConathy et al., Applied Radiation and Isotopes, 2003, 58, p. 657-666).

A solution prepared by dissolving 72.8 g (corresponding to 0.413 mole) of 3-benzyloxycyclobutane-1-one in 2.86 L of ethanol was added dropwise to a solution prepared by dissolving 397.0 g of ammonium carbonate and 88.4 g of ammonium chloride in 2.86 L of water, and the mixture was stirred at room temperature for 30 minutes. To the solution, 121.0 g of potassium cyanide was added and stirred at 60° C. overnight. The reaction solution was concentrated, and the resultant yellow solid was washed with 1.06 L of water to remove salts. The solid was subjected to azeotropic distillation with 927 mL of methanol and then purified by silica gel chromatography (elution solvent: dichloromethane/methanol=98/2) to produce anti-5-(3-benzyloxycyclobutane)hydantoin in 11.9% yield.

984 mg (corresponding to 4 mmol) of the synthesized anti-5-(3-benzyloxycyclobutane)hydantoin was dissolved in 50 mL of a saturated barium hydroxide solution and heated under reflux for 20 hours under closed conditions (the temperature of the oil bath was about 110° C.). After stirring the solution, 10 mL of 1 mol/L hydrochloric acid was added, and the solution was filtered. The filtrate was concentrated to yield anti-1-amino-3-benzyloxycyclobutane-1-carboxylic acid as white crystals (yield: 971 mg).

663 mg of anti-1-amino-3-benzyloxycyclobutane-1-carboxylic acid was dissolved in 80 mL of dehydrated toluene, and 42 μL (corresponding to 0.3 mmol) of triethylamine and 444 mg (corresponding to 3 mmol) of phthalic anhydride were added to the solution in an atmosphere of argon, followed by heating under reflux for five hours (the temperature of the oil bath was about 140° C.). Then, the reaction solution was concentrated to yield anti-1-amino-3-benzyloxycyclobutane-1-carboxylic acid as light yellow oily matter (yield: 896 mg).

896 mg of the resultant anti-1-amino-3-benzyloxycyclobutane-1-carboxylic acid was dissolved in 50 mL of mixed solution of dehydrated methanol/dehydrated tetrahydrofuran (1:1) in an atmosphere of argon, and 3 mL (corresponding to 6 mmol) of (trimethylsilyl)diazomethane was added and stirred at room temperature for 3 hours. Then, the reaction solution was concentrated and purified by silica gel chromatography (elution solvent: hexane/ethyl acetate=3/1) to yield anti-1-(N-phthalimide)-3-benzyloxycyclobutane-1-carboxylic acid methyl ester (yield: 855 mg).

The $^1$H NMR measurement results of the resultant compound were as follows.

$^1$H-NMR (CDCl$_3$, 500 MHz): δ 7.83-7.71 (m, 4H), 7.34-7.26 (m, 5H), 4.47 (s, 2H), 4.23-4.17 (q, 2H), 3.73 (s, 3H), 3.58-3.54 (m, 2H), 2.95-2.90 (m, 2H)

Then, 160 mg (corresponding to 0.4 mmol) of the synthesized anti-1-(N-phthalimide)-3-benzyloxycyclobutane-1-carboxylic acid methyl ester was dissolved in 35 mL of dehydrated methanol, and 35 mg of palladium-on-activated carbon (palladium content was 10%) was added to the solution and stirred at room temperature in an atmosphere of hydrogen for 5 hours. After that, the solution was filtered through Celite, and the filtrate was concentrated and then purified by silica gel chromatography (elution solvent: hexane/ethyl acetate=2/1) to yield anti-1-(N-phthalimide)-3-hydroxycyclobutane-1-carboxylic acid methyl ester (yield: 96 mg).

The $^1$H NMR measurement results of the resultant anti-1-(N-phthalimide)-3-hydroxycyclobutane-1-carboxylic acid methyl ester were show bellow.

$^1$H-NMR (CDCl$_3$, 500 MHz): δ 7.86-7.75 (m, 4H), 4.42 (broad s, 1H), 3.85-3.83 (q, 2H), 3.76 (s, 3H), 3.43-3.39 (m, 2H), 2.87-2.83 (m, 2H)

Then, 90 mg (corresponding to 0.3 mmol) of anti-1-(N-phthalimide)-3-hydroxycyclobutane-1-carboxylic acid methyl ester was dissolved in 33 mL of dehydrated methylene chloride, and 1.2 mL (14 mmol) of pyridine and 410 μL (corresponding to 2.4 mmol) of trifluoromethanesulfonic acid anhydride were added to the solution in an ice bath in an atmosphere of argon and stirred in the same ice bath for 30 minutes. After that, 33 mL of water was added to the reaction solution, and then 33 mL of 1 mol/L hydrochloric acid and 33 ml of water were added and allowed to stand to undergo separation. The resultant organic layer was concentrated and purified by silica gel chromatography (elution solvent: hexane/ethyl acetate=2/1) to yield anti-1-(N-phthalimide)-3-[[(trifluoromethyl)sulfonyl]oxy]-cyclobutane-1-carboxylic acid methyl ester (yield: 124 mg). The total yield was about 62%.

The $^1$H NMR measurement results of the yielded anti-1-(N-phthalimide)-3-[[(trifluoromethyl)sulfonyl]oxy]-cyclobutane-1-carboxylic acid methyl ester were shown below.

$^1$H-NMR (CDCl$_3$, 500 MHz): δ 7.88-7.70 (m, 4H), 5.42-5.36 (q, 1H), 3.87-3.83 (m, 2H), 3.79 (s, 3H), 3.36-3.31 (m, 2H)

Example 2

Synthesis of syn-1-amino-3-fluorocyclobutane-1-carboxylic acid

To make sure that syn-FACBC can be produced by the production process of the present invention, an experiment of synthesizing syn-1-amino-3-fluorocyclobutane-1-carboxylic acid using nonradioactive fluorine was performed.

A synthetic scheme of syn-1-amino-3-fluorocyclobutane-1-carboxylic acid is shown in FIG. 2.

146 mg (corresponding to 0.4 mmol) of anti-1-(N-phthalimide)-3-[[(trifluoromethyl)sulfonyl]oxy]-cyclobutane-1-carboxylic acid methyl ester was dissolved in 2.6 mL of 1,2-dichloroethane, and 164 μL (corresponding to 1 mmol) of trimethylamine trihydrofluoride and 165 μL (corresponding to 1.2 mmol) of triethylamine were added to the solution and heated under reflux for 3 hours in an atmosphere of argon (the temperature of the oil bath was about 90° C.). To the reaction solution, 50 mL of chloroform was added to dilute the solution, and 100 mL of water was added to the solution and allowed to stand to undergo separation. The resultant organic layer was concentrated and then purified by silica gel chromatography (elution solvent: hexane/ethyl acetate=2/1) to yield syn-1-(N-phthalimide)-3-fluorocyclobutane-1-carboxylic acid methyl ester (yield: 97 mg).

To 29 mg (corresponding to 0.1 mmol) of the yielded syn-1-(N-phthalimide)-3-fluorocyclobutane-1-carboxylic acid methyl ester, 200 μL of hydrazine hydrate and 1 mL of water were added and heated under reflux at 75° C. for 2 hours. After that, the reaction solution was concentrated and purified by preparative HPLC to yield syn-1-amino-3-fluorocyclobutane-1-carboxylic acid (yield: 14 mg).

The $^1$H NMR and $^{19}$F NMR measurement results of the yielded syn-1-amino-3-fluorocyclobutane-1-carboxylic acid were as follows.

$^1$H-NMR (D$_2$O, 500 MHz): δ 5.37-5.21 (dq, 1H), 3.14-3.08 (m, 2H), 2.76-2.68 (m, 2H)

$^{19}$F-NMR (D$_2$O, 500 MHz): δ-164.77 (dtt, J=50.6, 25.29, 9.48 Hz)

Example 3

Synthesis of syn-[$^{18}$F]-FACBC

The synthetic scheme of syn-[$^{18}$F]-FACBC is shown in FIG. 3.

0.2 mL of radioactive fluorine-containing H$_2$$^{18}$O enriched water (radioactivity: 193.7 MBq) prepared by subjecting H$_2$$^{18}$O enriched water (with $^{18}$O concentration of 99.9% or more) to proton bombardment was allowed to pass through a column packed with 0.5 mL of strongly acidic cation exchange resin (AG50W-X8, BIO RAD) and then pass through a column packed with 0.2 mL of weakly basic anion exchange resin (AG4-X4, BIO RAD). Then, 0.3 mL of 66 mmol/L potassium carbonate solution was allowed to pass through the above weakly basic anion exchange resin to elute [$^{18}$F]fluoride ions adsorbed on the weakly basic anion exchange resin, and the eluate was collected in a 5 mL glass vial.

Then, to the eluate, 1.5 mL of solution prepared by dissolving 13.3 mg (corresponding to 35.4 μmol) of Kryptofix 222 (under trade name, manufactured by Merck) in 1 mL of acetonitrile was added and heated at 110° C. for 10 minutes in a stream of Ar gas to evaporate water and acetonitrile. Then, the operation of adding 1 mL of acetonitrile and heating at 110° C. for 5 minutes was repeated twice so that the eluate was evaporated to dryness. To the resultant residue, a solution prepared by dissolving 16 mg (corresponding to 40 μmol) of anti-1-(N-phthalimide)-3-[[(trifluoromethyl)sulfonyl]oxy]-cyclobutane-1-carboxylic acid methyl ester in 1 mL of acetonitrile was added and heated at 80° C. for 15 minutes. The operation of concentrating the reaction solution, adding 3 mL of diethyl ether to the concentrated solution and then allowing the solution to pass through Silica Sep Pak (under trade name, manufactured by Japan Waters) was repeated twice to yield a solution of syn-1-(N-phthalimide)-3-[$^{18}$F]fluorocyclobutane-1-carboxylic acid methyl ester in diethyl ether (radioactivity (in terms of radioactivity at the time of starting the production): 76.8 MBq).

The yielded solution of syn-1-(N-phthalimide)-3-[$^{18}$F] fluorocyclobutane-1-carboxylic acid methyl ester in diethyl ether was concentrated, and 100 μL of hydrazine hydrate was added and stirred at 75° C. for 10 minutes for deprotection to yield syn-[$^{18}$F]-FACBC.

The reaction solution was subjected to TLC under the conditions described below, and the radiochemical purity was obtained using the following expression (1). The obtained radiochemical purity of the syn-[$^{18}$F]-FACBC was 96.9%.

$$RCP=RA_1/RA_t \times 100 \qquad (1)$$

in which RCP denotes radiochemical purity (%), RA$_1$ denotes radioactivity of syn-[18F]-FACBC peak, and RA$_t$ denotes the total radioactivity on TLC plate.

TLC Analysis Conditions
Mobile phase: acetonitrile/water/methanol/ethyl acetate=20/5/5/1
TLC plate: Silica Gel 60F254 (trade name, layer thickness: 0.25 mm, manufactured by Merck & Co., Inc.)
Development length: 10 cm

INDUSTRIAL APPLICABILITY

The present invention can be utilized in the field of nuclear medicine because it is useful for selectively producing a radioactive halogen-labeled syn-1-amino-3-halocyclobutane-carboxylic acid which can be used as a radiopharmaceutical.

Figure 1:
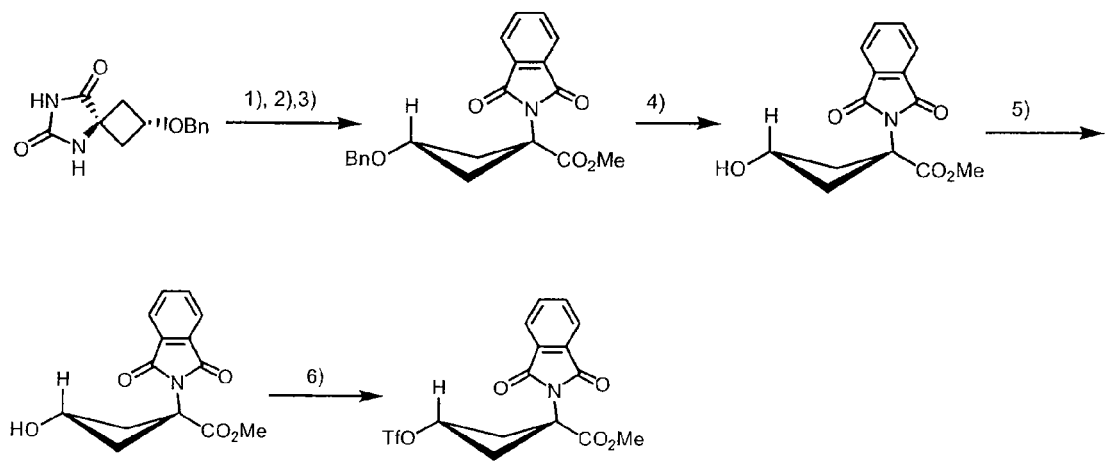
FIG. 1 shows a scheme of Example 1.
Figure 2:
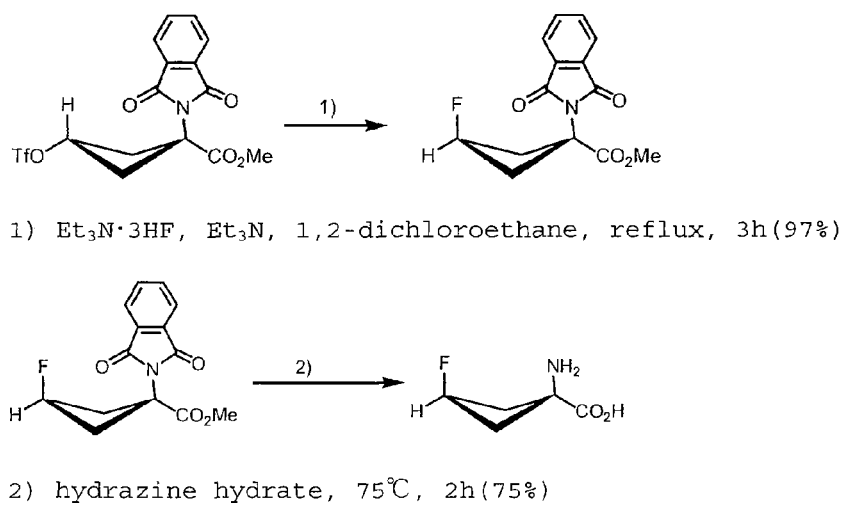
FIG. 2 shows a scheme of Example 2.
Figure 3:
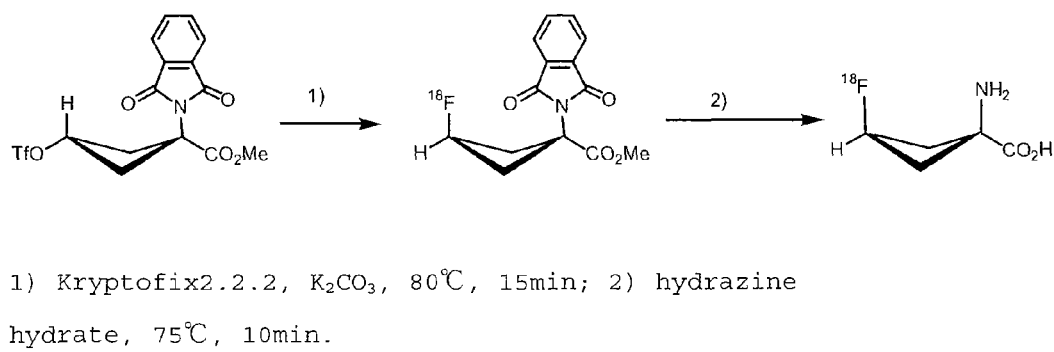
FIG. 3 shows a scheme of Example 3.

The invention claimed is:
1. An organic compound represented by the following formula

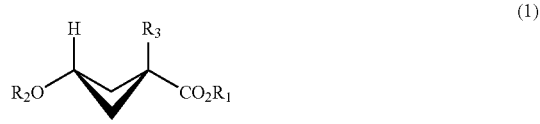

(1)

wherein
R$_1$ is a straight-chain or branched-chain alkyl group with one to 10 carbon atoms or an aromatic group;
R$_2$ is a straight-chain or branched-chain haloalkylsulfonic acid group with one to 10 carbon atoms, a straight-chain or branched-chain alkylsulfonic acid group with one to 10 carbon atoms, or an aromatic sulfonic acid group; and $R_3$ is a cyclic imide group.

2. An organic compound according to claim 1, wherein the cyclic imide group is a 5-membered ring cyclic imide.

3. An organic compound according to claim 1 or 2, wherein the cyclic imide group is a carbocyclic dicarboximide, an aliphatic saturated dicarboximide or an aliphatic unsaturated dicarboximide.

4. An organic compound according to claim 1, wherein the cyclic imide group is dithiasuccinimide, succinimide or phthalimide.

5. A process for producing a radioactive halogen-labeled organic compound of formula (3) comprising the steps of:

incorporating a radioactive halogen atom into the carbon atom at position 3 of a compound represented by the following formula (1):

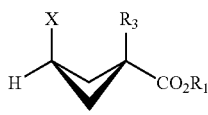

(1)

wherein $R_1$ is a straight-chain or branched-chain alkyl group with one to 10 carbon atoms, or an aromatic group;

$R_2$ is a straight-chain or branched-chain haloalkylsulfonic acid group with one to 10 carbon atoms, a straight-chain or branched-chain alkylsulfonic acid group with one to 10 carbon atoms, or an aromatic sulfonic acid group; and $R_3$ is a cyclic imide group, to obtain a compound represented by the following formula (2):

(2)

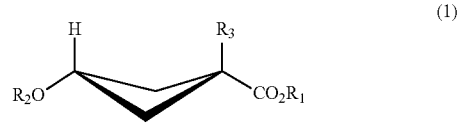

wherein X is a radioactive halogen substituent; $R_1$ is a straight-chain or branched-chain alkyl chain with one to 10 carbon atoms, or an aromatic group; and $R_3$ is a cyclic imide group; and deprotecting the above obtained compound to yield a compound represented by the following formula (3):

(3)

wherein X represents a radioactive halogen group.

6. A process for producing a radioactive halogen-labeled organic compound, according to claim 5, wherein the deprotecting step is conducted by subjecting a solution containing a compound represented by the following formula (2):

(2)

wherein X represents a radioactive halogen group; $R_1$ is a straight-chain or branched-chain alkyl chain with one to 10 carbon atoms, or an aromatic group; and $R_3$ is a cyclic imide group, to an acidic condition.

7. A process for producing a radioactive halogen-labeled organic compound, according to claim 6, wherein the acidic conditions are provided by adding an acid to the solution containing a compound represented by the following formula (2):

(2)

wherein X represents a radioactive halogen substituent; $R_1$ is a straight-chain or branched-chain alkyl chain with one to 10 carbon atoms, or an aromatic group; and $R_3$ is a cyclic imide group.

8. A process for producing a radioactive halogen-labeled organic compound, according to claim 7, wherein the acid added is an acid selected from the group consisting of hydrochloric acid, sulfuric acid, methanesulfonic acid, formic acid and acetic acid.

9. A process for producing a radioactive halogen-labeled organic compound, according to claim 5, wherein the deprotecting step comprises the steps of:

subjecting a solution containing a compound represented by the following formula (2):

(2)

wherein X represents a radioactive halogen group; $R_1$ is a straight-chain or branched-chain alkyl chain with one to 10 carbon atoms, or an aromatic group; and $R_3$ is a cyclic imide substituent, to a reducing condition so as to deprotect the cyclic imide group; and carrying out hydrolysis so as to deprotect the carboxylic acid ester.

10. A process for producing a radioactive halogen-labeled organic compound, according to claim 9, wherein the reducing condition is provided by adding a reducing agent to the solution containing a compound represented by the following formula (2):

(2)

wherein X represents a radioactive halogen substituent; $R_1$ is a straight-chain or branched-chain alkyl chain with one to 10 carbon atoms, or an aromatic group; and $R_3$ is a cyclic imide group.

11. A process for producing a radioactive halogen-labeled organic compound, according to claim 10, wherein the reducing agent added is an agent selected from the group consisting of hydrazine, methylhydrazine, phenylhydrazine, ethylenediamine and sodium borohydride.

12. An organic compound according to claim 3, wherein said cyclic imide substituent is a carbocyclic dicarboximide group.

13. An organic compound according to claim 3, wherein said cyclic imide substituent is an aliphatic saturated dicarboximide group.

14. An organic compound according to claim 3, wherein said cyclic imide substituent is an aliphatic unsaturated dicarboximide group.

15. An organic compound according to claim 1, wherein in the cyclic imide is succinimide.

16. An organic compound according to claim 1, wherein the cyclic imide is phthalimide.

* * * * *